United States Patent
Schendell-Gröling (10) Patent No.: US 7,044,733 B2
(45) Date of Patent: May 16, 2006

(54) MOUNTING AID FOR MOUNTING AN ORTHODONTIC BRACKET TO A TOOTH

(76) Inventor: Claus Schendell-Gröling, Apostelholzweg 9, D-82205 Gllching (DE)

( * ) Notice: Subject to any disclaimer, the term of this patent is extended or adjusted under 35 U.S.C. 154(b) by 307 days.

(21) Appl. No.: 10/600,374

(22) Filed: Jun. 20, 2003

(65) Prior Publication Data

US 2004/0013992 A1    Jan. 22, 2004

(30) Foreign Application Priority Data

Jun. 20, 2002  (EP)  ................................. 02013758

(51) Int. Cl.
 *A61C 3/00* (2006.01)
(52) U.S. Cl. .......................................................... 433/3
(58) Field of Classification Search .................... 433/3, 433/8, 9, 24
See application file for complete search history.

(56) References Cited

U.S. PATENT DOCUMENTS

| | | | | |
|---|---|---|---|---|
| 3,521,355 A | * | 7/1970 | Pearlman ......................... | 433/3 |
| 3,787,976 A | * | 1/1974 | Cohen ............................. | 433/3 |
| 4,523,908 A | * | 6/1985 | Drisaldi et al. ................. | 433/8 |
| 4,626,208 A | * | 12/1986 | Hall ................................ | 433/3 |
| 5,542,842 A | | 8/1996 | Andreiko et al. | |
| 6,123,544 A | | 9/2000 | Cleary | |
| 6,565,355 B1 | * | 5/2003 | Kim et al. ...................... | 433/3 |
| 2003/0224310 A1 | * | 12/2003 | Andreiko ........................ | 433/3 |

OTHER PUBLICATIONS

European Patent Office; European Search Report; Nov. 7, 2002.

* cited by examiner

*Primary Examiner*—Todd E. Manahan
(74) *Attorney, Agent, or Firm*—Jansson, Shupe, Munger & Antaramian (57) ABSTRACT

A mounting aid for positioning an orthodontic bracket on a tooth is provided. The aid comprises a sheet strip having an abutment portion for the positive engagement at the bracket, a holding portion for anchoring at the sheet strip an elastomeric tensioning device attached to the bracket, and a lug extending away from the holding portion. The lug is embedded in casting compound made to form a small cap of the tooth to be aligned using Hiro technology. A mounting gauge formed of the mounting aid and the small cap can non-destructively be removed from the bracket after attachment of the bracket on the tooth by means of the mounting aid. If the bracket shall detach from the tooth in the course of the orthodontic treatment, the mounting gauge can be used for positioning the bracket when newly attaching same on the tooth.

13 Claims, 7 Drawing Sheets

MOUNTING AID FOR MOUNTING AN ORTHODONTIC BRACKET TO A TOOTH

RELATED APPLICATION

This application claims the benefit of EP 02 013 758.4, filed on Jun. 20, 2002. The contents of which are incorporated herein.

FIELD OF THE INVENTION

This invention is related generally to orthodontic brackets and, more particularly, to mounting aids for positioning orthodontic brackets in a reproducible manner.

BACKGROUND OF THE INVENTION

The correction of misalignments in teeth is achieved by the aid of brackets. The brackets are adhered onto the teeth of the respective jaw of the patient in predetermined positions and are subsequently joined with one another by a resilient arch wire. The brackets are applied to the individual teeth in a position that is selected so that at the end of the orthodontic treatment the arch wire extending through the brackets is substantially free from undulations. At the beginning of the treatment, the arch wire therefore has a very complex extension. The relatively large arch wire following the jaw is, depending on the misalignment of the teeth, more or less undulated within and outside the plane defined by the arch wire.

Two fundamental methods exist to determine the correct position of the brackets on the teeth to which they are to be adhered. One of these methods requires an optical measuring of the jaw. The measured data collected is then subsequently processed by the aid of a computer program which does not only determine the bracket position but also controls a wire bending machine. By means of the wire bending machine, a set of arch wires of different cross sections is bent to relatively complex shapes which take the individual misalignment of the teeth into consideration. This technique is particularly useful where lingual brackets are desired since the shapes of teeth on their lingual side may differ from individual to individual, making orientation difficult with respect to the contour of the tooth crown. This is different from the image of the crown on the labial side where teeth have essentially matching shapes despite the individuality of human beings.

The above-mentioned computer technology is extremely expensive. It requires an investment on the scale of EUR 100,000 to EUR 120,000 for machines and programs. In view of the relatively small number of orthodontic treatments using lingual brackets, the acquisition of such equipment is inefficient for the individual orthodontist. As a matter of fact, less than 10 computers of this type are being used worldwide at present.

The conventional method of defining bracket positions on teeth is the so-called Hiro technology. In accordance with this technology, the orthodontist first makes a dental impression of the denture to be corrected. From this impression the dental technician prepares a plaster cast of the denture to be corrected. The cast taken from the impression is sawed into individual teeth that are subsequently reassembled by means of wax in a manner replicating the perfect occlusion sought to be achieved by the orthodontic treatment.

Afterwards, the arch wire is made. Brackets are attached onto the arch wire and the wire is positioned together with the brackets on the lingual side of the corrected plaster cast in a way where the brackets oppose the teeth in a predetermined manner. A predetermined distance is kept between the base plates of the brackets and the teeth since this shall later be filled by a casting compound.

Individual small caps are formed from a light-curing acrylic resin over the incisal edge of each tooth, these caps extending to the brackets and adhering thereto. After curing of the small caps, the brackets are removed from the arch wire. Then, the small caps with the brackets hanging thereon are individually set onto the teeth of the corrected plaster cast. The gaps between the base plates of the brackets and the tooth crowns are filled by a curing casting compound, forming a so-called individual base for each bracket. It is self-evident that a separating agent is used at the teeth of the corrected cast to prevent adhesion of the casting compound to the teeth.

After completion of this preparatory laboratory work, the set of brackets is adhered by the orthodontist using a thin adhesive film onto the corresponding teeth of the denture to be corrected on the patient. Here the small caps again serve as gauges to position the brackets on the teeth in the same manner as they had been positioned on the corrected plaster cast. After curing of the adhesive, the small caps are then broken off. This is an elaborate job, since the acrylic material must be removed completely from the brackets.

A problem with this procedure is that, after an unintended release of a bracket from a tooth sometime during the orthodontic correction treatment, it is difficult to correctly re-attach the respective bracket onto the tooth. This work can only be carried out with the assistance of a laboratory. When using a computerized measurement, a completely new measurement is required. A new set of wires must be made, since the patient usually does not immediately consult his/her orthodontist and the alignment correction may have, in the meantime, reset itself. With the Hiro technology, a new individual base including an acrylic cap must be manufactured in the laboratory for the new bracket.

The unintended release of a bracket is not rare. It usually occurs at least once with every patient during the duration of the treatment.

SUMMARY OF THE INVENTION

The object of the invention is to provide a remedy to the above disadvantages and to provide a device by means of which it is possible to re-attach a bracket released from a tooth without the aid of a dental technician in the laboratory.

The solution achieved by the invention is carried out by a mounting aid that attaches to an orthodontic bracket for a tooth. The mounting aid comprises a sheet strip having an abutment portion positively engaging the bracket, a holding portion for anchoring a resilient tensioning device at the sheet strip to secure the sheet strip to the bracket, and a lug projecting away from the holding portion.

This mounting aid improves the Hiro technology in a manner where destruction of the above-mentioned acrylic caps is avoided since these small caps can be saved for when there is a need later to re-attach brackets that detach.

The procedure when using the invention is as follows. In the manner common for Hiro technology, a dental impression is first of all taken of the denture. Then, a cast is taken from this dental impression and this cast is sawed into pieces. The individual teeth of the cast are reassembled for perfect occlusion and then the arch wire is made, as explained before. Before the brackets are re-attached to the arch wire, or thereafter, the mounting aid according to this invention is fixed to each bracket. This mounting aid is designed in a manner whereby it connects to the bracket in a stable orientation. Its lug extends towards the direction of the occlusion plane of the tooth and preferably projects there beyond. Then, the caps are formed at the teeth in a conventional manner by using the light-curing acrylic resin. In a difference compared to known technology, however, the small caps are only embedded to the lugs and not to the bracket attached to the mounting aid. Afterwards, the acrylic resin is cured.

Further processing then achieves in the usual manner the manufacture of the individual base at each bracket. The bracket set finished in this manner is provided to the orthodontist together with the mounting aids attached thereto and embedded into the small caps. The orthodontist then positions the brackets at the misaligned teeth. The small caps with the mounting aid attached thereto thus form mounting gauges for the attachment of the brackets in predetermined positions on the teeth. With the bracket in position, the orthodontist adheres each bracket by means of a thin adhesive layer to the corresponding tooth. After curing of the adhesive layer, the orthodontist removes the mounting gauges from the brackets. It is not required to destroy anything for this purpose.

The orthodontist stores the mounting gauges since they are provided with individual marks to enable him/her to use them later, if necessary, when a bracket becomes unintentionally detached from a tooth.

The component according to the invention, i.e. the mounting aid, must of course be adapted to the type of the bracket used. This ensures that the bracket and the mounting aid take a predetermined position with respect to each other in a reproducible manner. The mounting aid according to the invention therefore comprises abutment means for the positive engagement at the bracket and holding means for anchoring a tensioning means that detachably fixes the mounting aid to the bracket. The tensioning means is firmly anchored at the mounting aid so that handling is facilitated. It may be an elastomeric O-ring or a spring, such as a spring ring, a strap spring or a coil spring having loops at its ends.

In one embodiment of this invention, the tensioning device, for instance the above-mentioned O-ring, is attached directly to the bracket structure. In an alternative embodiment, an anchoring member is provided to hold the tensioning device, particularly the tension ring. The anchoring device is preferably in the form of a hook and most preferably holds the tensioning device in a captive manner. This anchoring member is attached to the bracket in a manner where the member can later be released from the bracket. The anchoring member may for instance engage the bracket frame from above it. It may also be in a form that is inserted into an opening present on the locking spring of a self-ligating bracket. The opening is usually provided for inserting a tool by which the locking spring can be opened and closed by the orthodontist.

The lug on the sheet strip is preferably so long that is projects beyond the small cap after attaching to the small cap. It can then be easily held by means of tweezers or tongs. For this purpose, the lug may be wider at the end projecting from the small cap. It is also advantageous if the lug has laterally projecting noses since these improve the anchoring of the acrylic resin forming the small cap to the lug.

DETAILED DESCRIPTION OF PREFERRED EMBODIMENTS

The invention will now be described with reference to the embodiments shown in the drawings.

Figure 1:
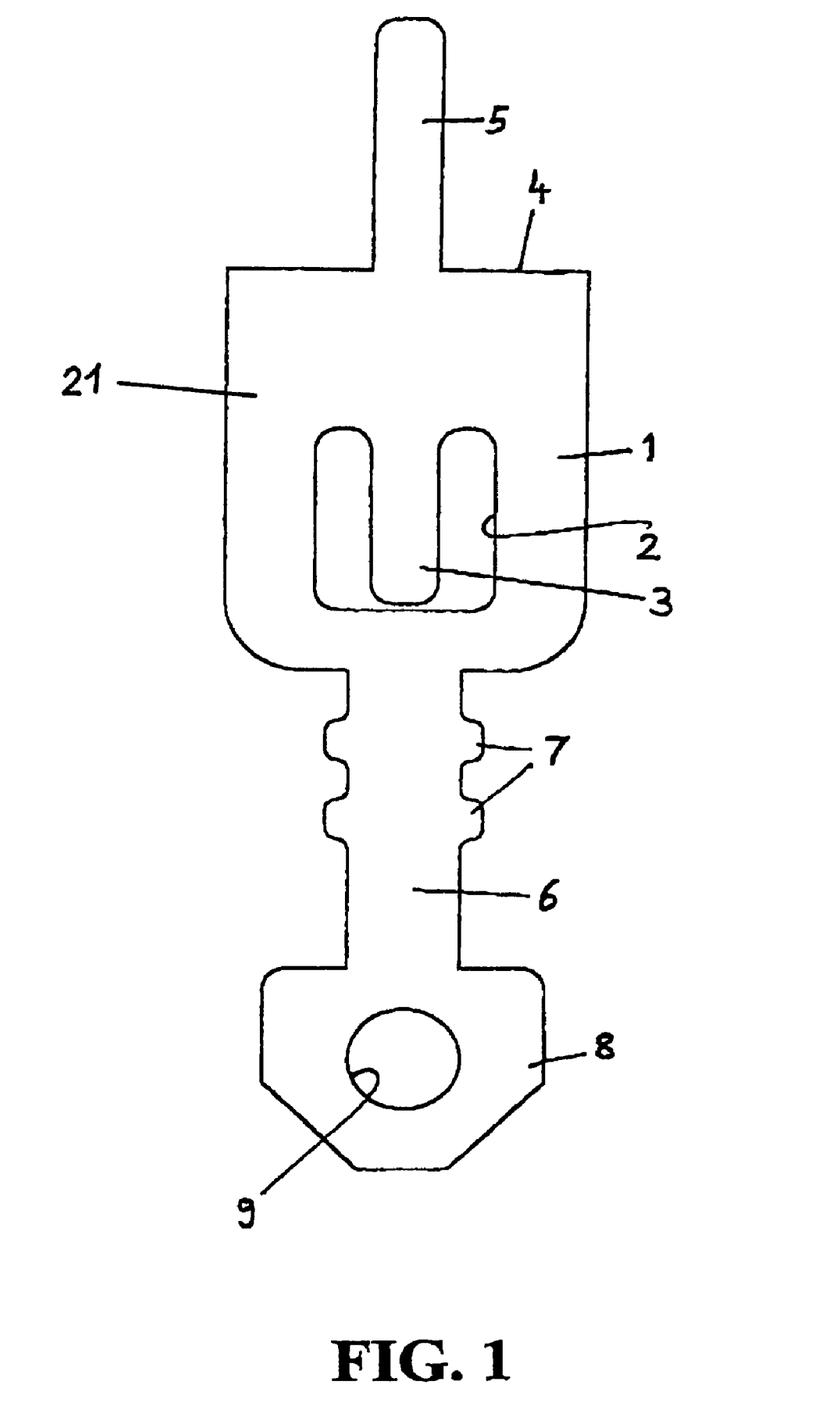
FIG. 1 is a top plan view of the sheet strip of a mounting aid according to a first embodiment of the invention.

FIG. 1 shows in a top plan view a first embodiment of a sheet strip 21 according to the invention on an enlarged scale. In this connection, it must be noted that brackets, for whose mounting the mounting aid according to the invention is directed, are relatively small components and, accordingly, the sheet strip 21 shown in FIG. 1 on a highly enlarged scale is also very small. Its overall length is for instance approximately 11.5 mm and the largest width is approximately 3.2 mm. Sheet strip 21 has a thickness of approximately 0.4 mm. The details of the component are therefore also small.

As seen in FIG. 1, sheet strip 21 comprises a base 1 in which an opening 2 is formed at whose edge begins a holding nose 3 extending from base 1. Holding nose 3 is directed to anchoring and holding an elastomeric O-ring 14 (not shown in FIG. 1). Base 1 has a straight front edge 4 from the center of which a tongue 5 extends, the end of which being rounded in the example shown. The transition between tongue 5 and front edge 4 is preferably a sharp edge in order not to affect the alignment of mounting aid 20 with bracket 22 when attached.

A lug 6 extends from the end of base 1 opposite to front edge 4, lug 6 taking almost half of the overall longitudinal extension of mounting aid 20. Lug 16 is provided with projecting noses 7 and has a widened head 8 at its end with a hole 9 being formed in head 8.

Figure 2:
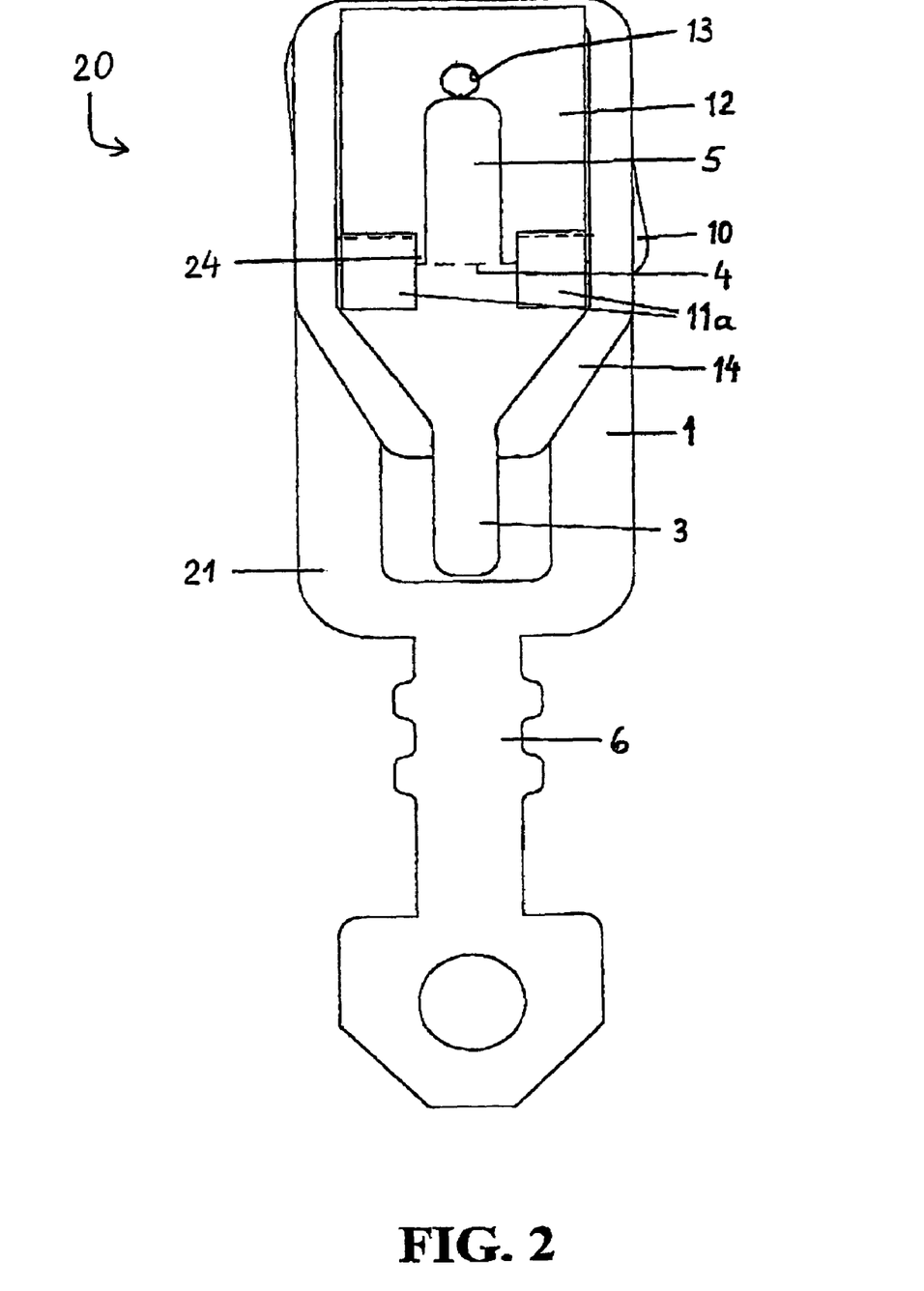
FIG. 2 is a top plan view of the mounting aid according to a first embodiment of the invention, showing the mounting aid fixed to a bracket.

FIG. 2 shows, in approximately the same scale as FIG. 1, mounting aid 20 in its position fixed to the bracket 22. The contour of a base plate 10 of bracket 22 can be recognized, base plate 10 extending obliquely with respect to frame 23 of bracket 22. A two-piece wing 11a of frame 23 can be seen in FIG. 2. Frame 23 is substantially covered by a locking leaf spring 12, which extends over a second wing 11b (FIG. 3) on frame 23. A bore 13 is provided in leaf spring 12. Bore 13 usually serves as an engagement point for an acute tool, by means of which the locking leaf spring 12 may be brought to its open position on bracket 22.

Frame 23 of bracket 22 is enclosed by an O-ring 14 on the side opposite from base 1, O-ring 14 being held on base 1 by means of holding nose 3. This elastomeric O-ring 14 secures sheet strip 21 to bracket 22. The details thereof can be seen more precisely in FIG. 3.

Figure 3:
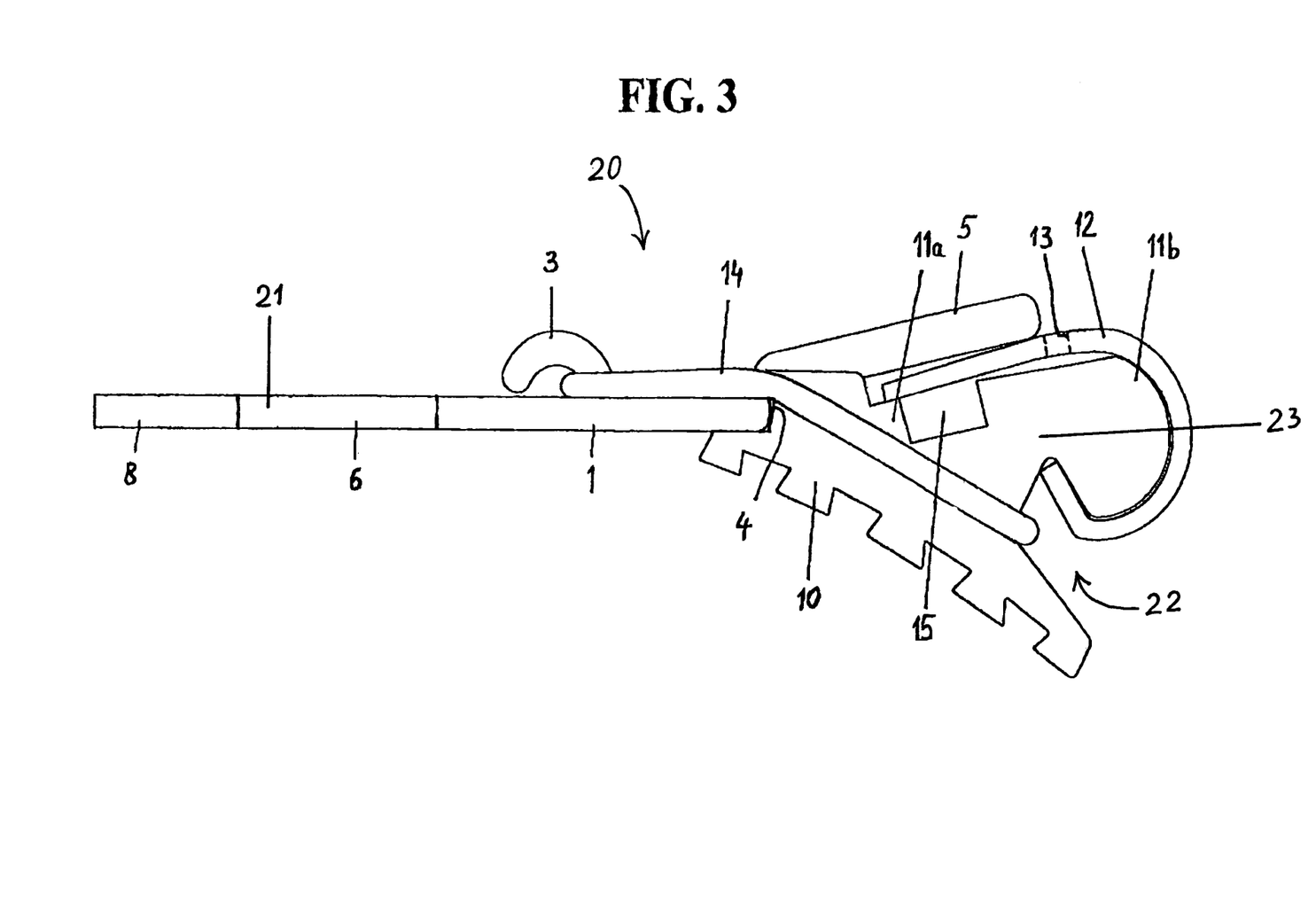
FIG. 3 is a side elevation of a bracket with a mounting aid according to FIG. 2 fixed to the bracket.

FIG. 3 shows bracket 22 from the side. Bracket 22 is substantially characterized by its base plate 10, frame 23 elevating thereon and leaf spring 12 covering an arch wire receiving slot 15. On both sides of slot 15, frame 23 is comprised of front and rear wings 11a and 11b, respectively. Rear wing 11b, as already mentioned, is enclosed by locking leaf spring 12. Front wing 11a is provided with an undercut 16 on its side opposite from slot 15. Undercut 16 is hardly visible in FIG. 3 since it is covered by O-ring 14, but it can better be seen in the embodiment of the invention according to FIG. 4. Undercut 16 is provided in bracket 22 for possibly also receiving a ligature (not shown) that would encircle both wings 11a and 11b and extend over an arch wire (not shown) inserted into slot 15 and would serve to increase the effect of spring 12 on the arch wire within slot 15.

Front wing 11a is, as may clearly be seen in FIG. 2, provided with a gap 24 in its center and is therefore divided into two.

FIG. 3 illustrates mounting aid 20 according to the invention attached to bracket 22. Sheet strip 21 of mounting aid 20 is characterized by base 1, lug 6 and tongue 5. Base 1 contacts bracket 22 in a manner where its marginal portion adjoining edge 4 is positioned within undercut 16, wherein edge 4 abuts bracket 22. Tongue 5 extends through the entire gap 24 which is formed in front wing 11a and rests on leaf spring 12 which covers wire receiving slot 15. Holding nose 3 is formed in the shape of a loop that projects upwardly from base 1. The O-ring 14 is anchored at holding nose 3 and winds around frame 23 to pull sheet strip 21 towards bracket 22 so that edge 4 of base 1 firmly abuts bracket 22 within undercut 16. Tongue 5 prevents sheet strip 21 from pivoting upwards. Edge 4 in undercut 16, tongue 5 on leaf spring 12 (which is in a closed position), and O-ring 14 together form means to secure mounting aid 20 according to the invention in a well-defined, reproducible position with respect to bracket 22 from which mounting aid 20 can be released without destroying any components.

Figure 4:
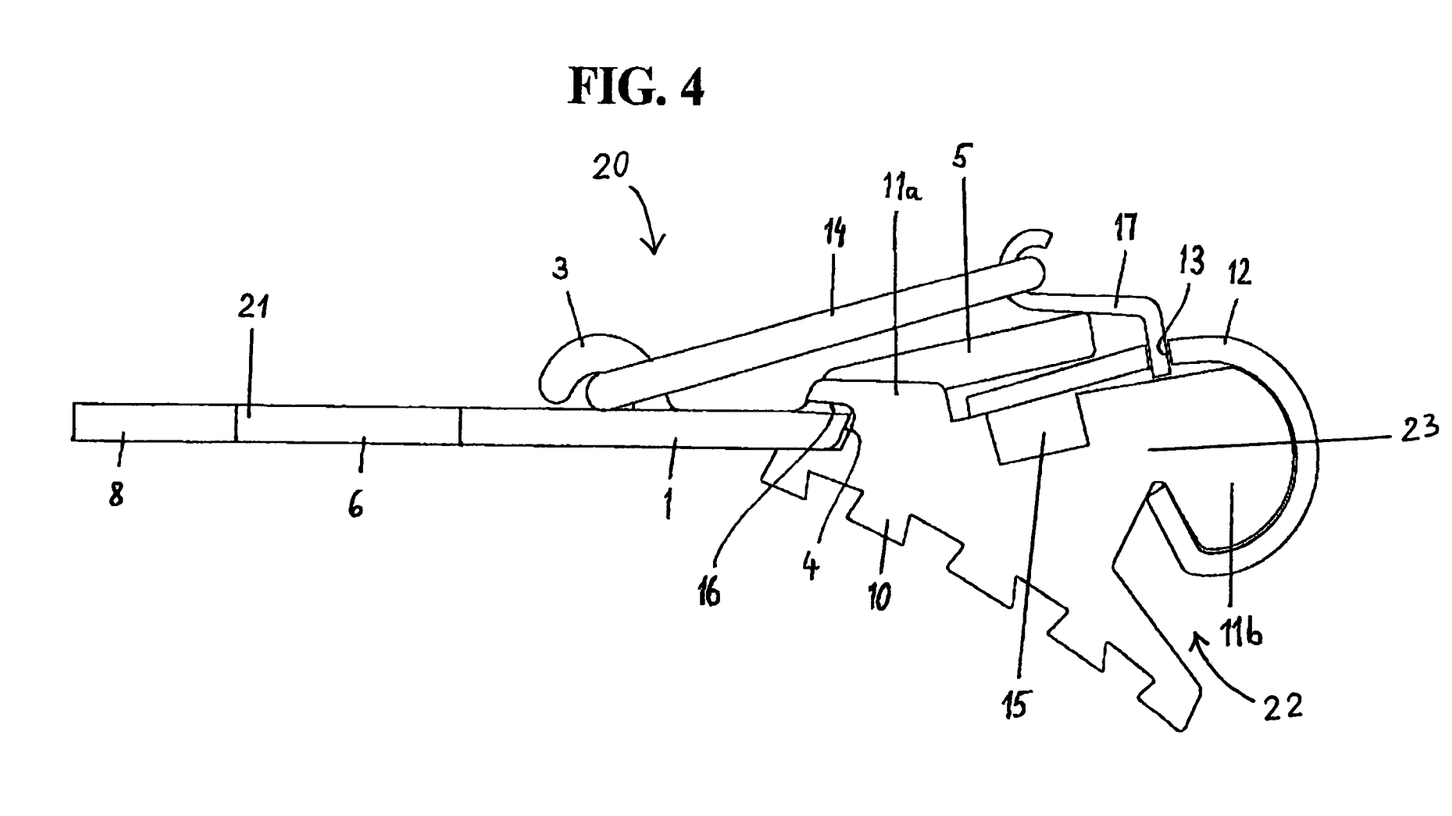
FIG. 4 is a side elevation of a bracket with a mounting aid similar to FIG. 2 fixed to the bracket, the mounting aid having an additional anchoring device.

FIG. 4 shows a modified embodiment of mounting aid 20 according to the invention. In this embodiment, O-ring 14 is not wound around frame 23 but is secured to a hook-shaped anchoring element 17 that is inserted into the already mentioned bore 13 in locking leaf spring 12 on bracket 22. The hook on anchoring element 17, on which O-ring 14 is attached, is preferably closed to the point that only a small gap remains. An open loop is thereby formed into which O-ring 14 can be drawn when stretched so that O-ring 14 is firmly held by anchoring element 17 as long as O-ring 14 does not break. It can be recognized that O-ring 14, which is held between sheet strip 21 and bracket 22, pulls sheet strip 21, as in the example according to FIG. 3, into a defined position. This is determined by edge 4 disposed in undercut 16 and tongue 5 resting on leaf spring 12.

Figure 5:
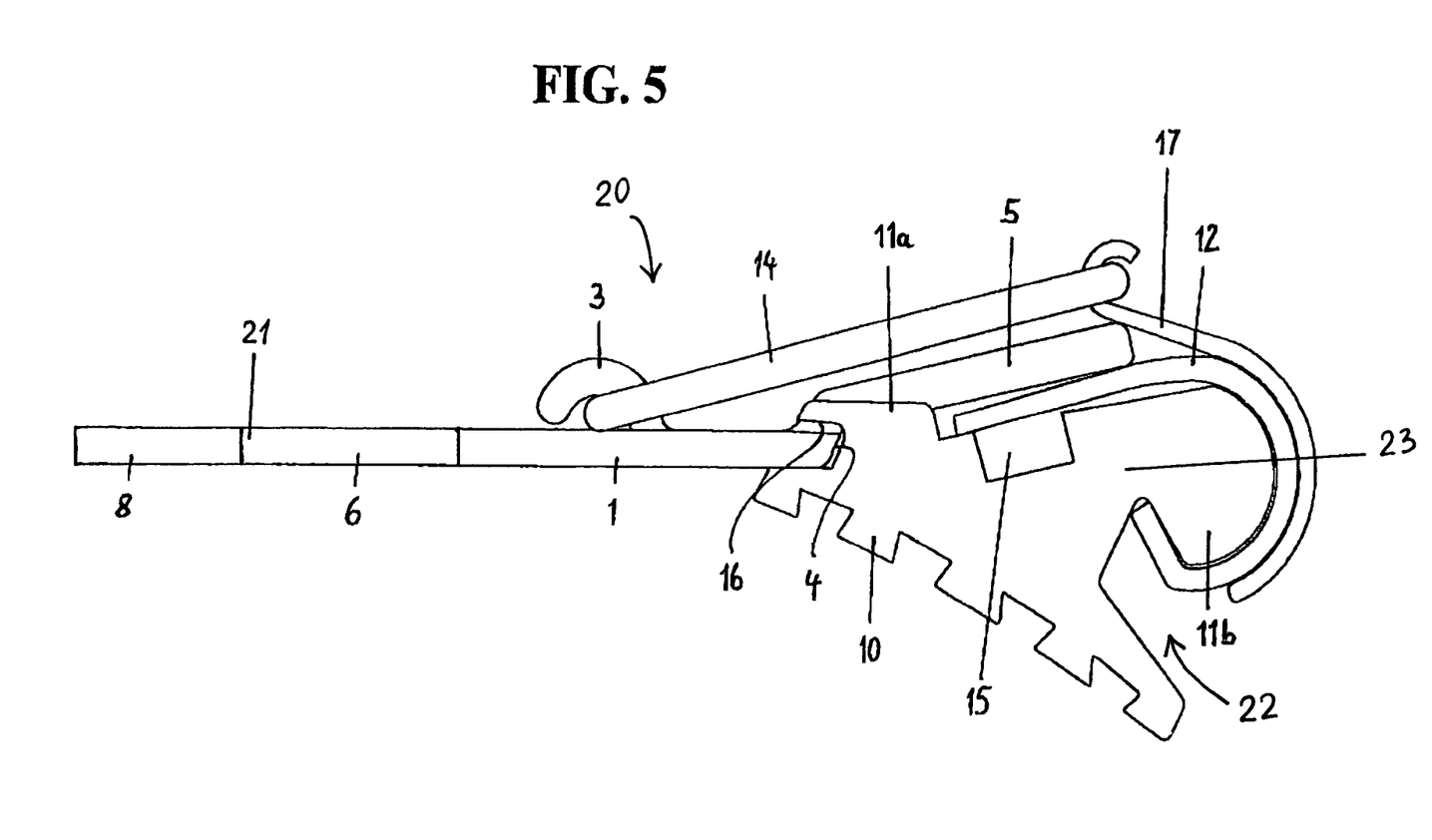
FIG. 5 is a side elevation of a bracket with a mounting aid similar to FIG. 2 fixed to the bracket, the mounting aid having a modified anchoring device.

FIG. 5 shows a further way how O-ring 14 can be anchored on bracket 22 so that it pulls sheet strip 21 to a predetermined position. The form of sheet strip 21 is similar to the embodiment seen in FIGS. 2 to 4. Comparable to the example illustrated in FIG. 4, however, this embodiment uses a hook-shaped anchoring element 17 to secure O-ring 14. Anchoring element 17, in this case, extends arcuately around rear wing 11b of the frame 23 and around locking leaf spring 12 partially encompassing rear wing 11b. In this embodiment, the hook at which O-ring 14 is anchored can also be substantially closed so as to form an open loop. O-ring 14 can then be drawn into this open loop only when placed under tension.

Figure 6:
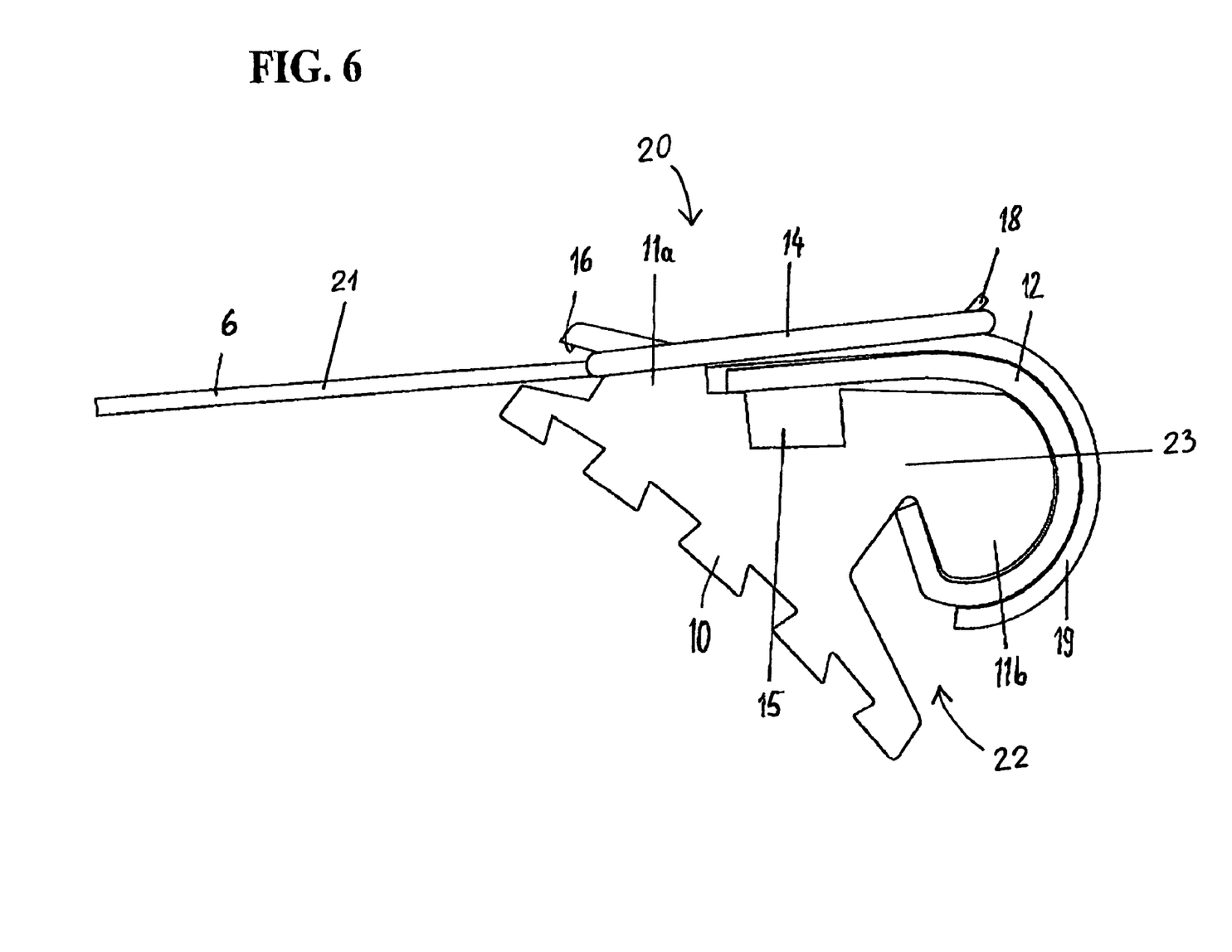
FIG. 6 is a side elevation of a bracket with a mounting aid fixed to the bracket according to a second embodiment of the invention.
Figure 7:
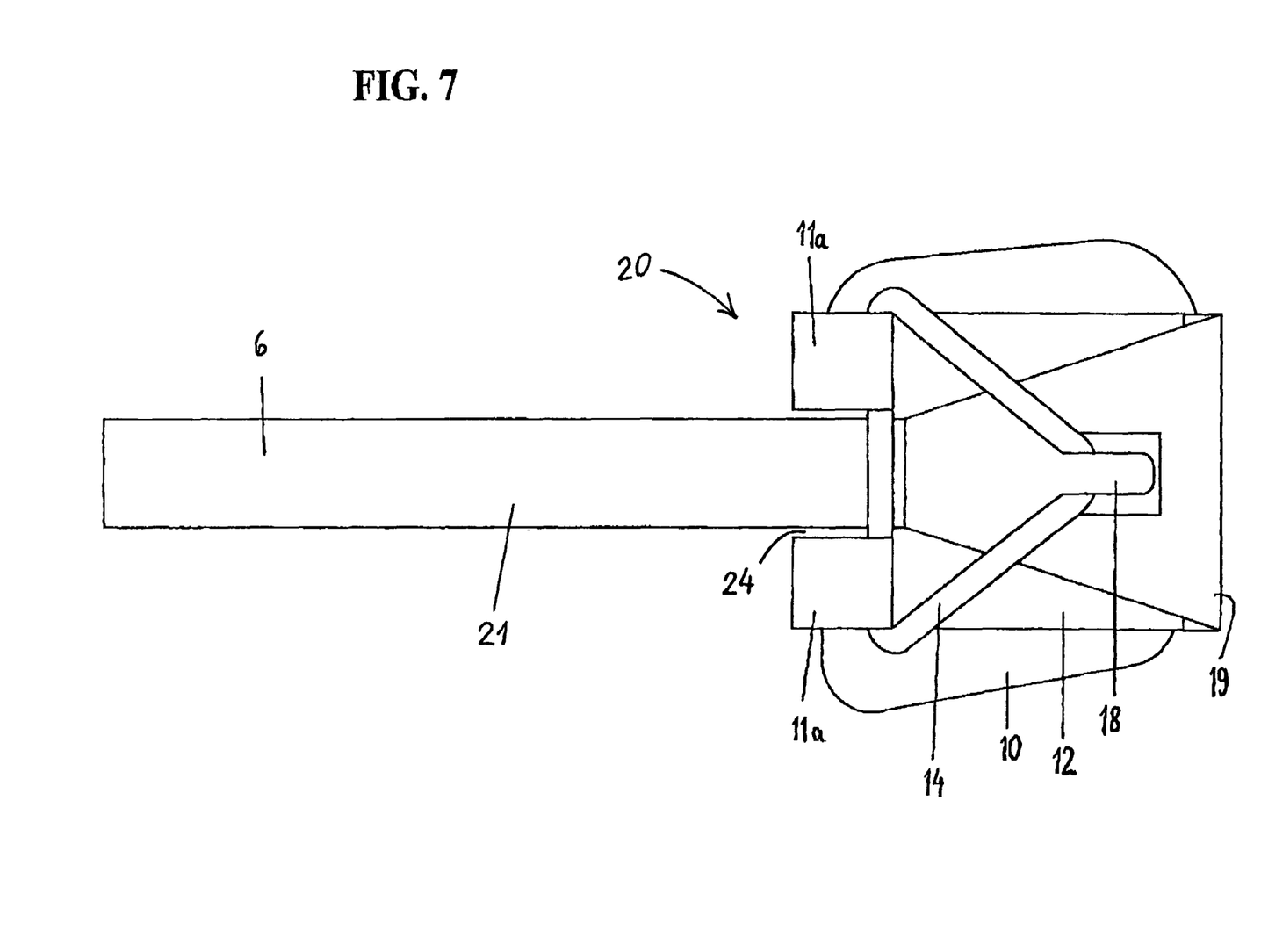
FIG. 7 is a top plan view of the arrangement of FIG. 6.

FIGS. 6 and 7 show a second embodiment of the invention that is adapted to a bracket 22 of a predetermined type. Mounting aid 20 of this embodiment includes a sheet strip 21 having a rear end formed in an arc 19. The inner contour of arc 19 is adapted to the outer contour of leaf spring 12 when leaf spring 12 is positioned on bracket 22 in its closed or locked position. Arc 19 rests on leaf spring 12. Arc 19 engages bracket 22 beneath rear wing 11b. Holding nose 18 extends upward from the upper side of sheet strip 21. At least in the area in which the split front wing 11a of the bracket 22 is located, sheet strip 21 is so narrow that it fits into gap 24 between the two members of front wing 11a as seen in FIG. 7. A lug 6 extends from there which is present to be embedded into acrylic resin for forming a small cap.

As shown in FIGS. 6 and 7, sheet strip 21 is secured by an elastomeric O-ring 14 to bracket 22, the O-ring 14 extending through undercut 16 at front wing 11a and being anchored at holding nose 18. O-ring 14 pulls sheet strip 21 into a defined position in which the inner side of arc 19 tightly abuts leaf spring 12 and base 1 connected to arc 19 rests on leaf spring 12.

The invention claimed is:

1. A mounting aid for positioning an orthodontic bracket to a tooth, comprising a sheet strip and a resilient tensioning device to secure the sheet strip to the bracket, the sheet strip having a holding member extending from an outer surface of the sheet strip for firmly holding the tensioning device to the sheet strip, an abutment portion extending forward a length from the holding member for positively engaging the bracket and having outer and inner surfaces substantially spaced apart along the length, and a lug extending rearward a length from the holding member and having outer and inner surfaces equally spaced apart along the length.

2. The mounting aid of claim 1 wherein the bracket has a frame and the abutment portion has a front edge extending between the outer and inner surfaces and a tongue extending from the edge, the edge being adapted to be received within an undercut beneath the frame and the tongue being adapted to engage the frame from above the frame and to extend through a gap defined by the frame.

3. The mounting aid of claim 2 wherein the resilient tensioning device is an elastomeric O-ring.

4. The mounting aid of claim 1 wherein the lug includes a plurality of projections.

5. The mounting aid of claim 1 wherein the lug includes a narrow proximal portion having side edges and a widened distal end extending orthogonally outward from the side edges.

6. A mounting aid for mounting an orthodontic bracket to a tooth comprising a sheet strip and a resilient tensioning means member adapted to secure the sheet strip to the bracket, the sheet strip including an abutment member adapted to positively engage the bracket, a holding member adapted to firmly hold the tensioning means to the sheet strip, and a lug extending away from the holding member.

7. The mounting aid of claim 6 wherein the bracket has a frame and the abutment member comprises an edge and a tongue, the edge being adapted to engage the frame from below the frame and the tongue being adapted to engage the frame from above the frame.

8. The mounting aid of claim 6 wherein the lug has a plurality of projections and a widened end, the end having a hole.

9. A mounting aid for positioning an orthodontic bracket to a tooth comprising a resilient tensioning device attachable with respect to the bracket, a sheet strip having an abutment portion for positively engaging the bracket, a holding portion for fastening the tensioning device to the sheet strip such that the tensioning device secures the sheet strip to the bracket, and a lug extending away from the holding portion, and an anchoring member adapted to attach to the bracket such that the anchoring member secures the tensioning device to the bracket.

10. The mounting aid of claim 9 wherein the anchoring member has an end that forms a hook.

11. The mounting aid of claim 9 wherein the anchoring member is adapted to firmly hold the tensioning device.

12. The mounting aid of claim 11 wherein the tensioning device is an elastomeric O-ring.

13. A mounting aid for positioning an orthodontic bracket to a tooth comprising a spring attachable with respect to the bracket and a sheet strip having an abutment portion for positively engaging the bracket, a holding portion for fastening the spring to the sheet strip such that the spring secures the sheet strip to the bracket, and a lug extending away from the holding portion, wherein the abutment portion has an edge adapted to engage a frame of the bracket from below the frame and a tongue adapted to engage the frame from above the frame.

* * * * *

UNITED STATES PATENT AND TRADEMARK OFFICE
CERTIFICATE OF CORRECTION

PATENT NO. : 7,044,733 B2  
APPLICATION NO. : 10/600374  
DATED : May 16, 2006  
INVENTOR(S) : Claus Schendell-Groling Page 1 of 1

It is certified that error appears in the above-identified patent and that said Letters Patent is hereby corrected as shown below:

In the Summary of the Invention:

Column 3, line 56, delete the word "is" and replace with the word --it--.

In the Claims:

Column 6, line 18, delete the "," after the word "tooth".
Column 6, line 24, add the word --equally-- after "substantially".
Column 6, line 45, delete the word "means".

Signed and Sealed this

Seventeenth Day of October, 2006

JON W. DUDAS
*Director of the United States Patent and Trademark Office*